United States Patent [19]
Smith, Jr. et al.

[11] Patent Number: 5,290,261
[45] Date of Patent: Mar. 1, 1994

[54] SYRINGE AMPULE HOLDING DEVICE

[76] Inventors: George F. Smith, Jr., 1 White Oak Mountain Rd., Columbus, N.C. 28722; Ann M. Rowe, 608 Spencer Cir., Spartanburg, S.C. 29302

[21] Appl. No.: 969,470

[22] Filed: Oct. 30, 1992

[51] Int. Cl.⁵ .................................. A61M 5/00
[52] U.S. Cl. ............................ 604/234; 433/49
[58] Field of Search .......... 604/232, 233, 234, 189, 604/311; 248/311.2, 315; 433/163, 49

[56] References Cited

U.S. PATENT DOCUMENTS

| | | | |
|---|---|---|---|
| 575,711 | 1/1897 | Haley | 248/315 |
| 845,739 | 3/1907 | Alson | 248/315 |
| 1,290,433 | 1/1919 | Walker . | |
| 1,462,108 | 7/1923 | Holywell | 401/131 |
| 1,545,452 | 3/1924 | Pinn . | |
| 1,709,637 | 4/1929 | Steuer | 604/234 |
| 1,718,592 | 6/1929 | Smith | 604/234 |
| 1,766,235 | 6/1930 | Wells | 433/163 |
| 1,817,652 | 8/1931 | Smith | 604/234 |
| 2,191,782 | 7/1937 | Valane . | |
| 2,222,741 | 11/1940 | Bush | 433/163 |
| 2,327,077 | 8/1943 | Teetor . | |
| 2,475,061 | 7/1949 | Smith | 604/234 |
| 2,627,269 | 2/1953 | McGregor . | |
| 2,677,372 | 5/1954 | Barnish, Jr. . | |
| 2,698,155 | 12/1954 | Bowman | 248/311.2 |
| 3,698,675 | 10/1972 | Lerew et al. | 248/311.2 |
| 3,881,677 | 5/1975 | Ihlenfeld . | |
| 3,945,596 | 3/1976 | Marraccini . | |
| 4,717,057 | 1/1988 | Porteous | 433/49 |
| 4,844,400 | 7/1989 | Jasmagy, Jr. | 248/311.2 |
| 4,878,642 | 11/1989 | Kirby, Jr. . | |
| 5,048,731 | 9/1991 | Moreschini | 433/163 |
| 5,112,227 | 5/1992 | Bull | 433/49 |

Primary Examiner—Paul J. Hirsch
Attorney, Agent, or Firm—Dority & Manning

[57] ABSTRACT

An ampule holder for supporting ampules on the body of a syringe is provided. The ampule holder includes an annular hollow cylindrical body with an inner circumference adapted to engage and support the ampule. The hollow body is held in abutting contact with the barrel of the syringe by an annular ring attached to the hollow body and extending about the body of the syringe. The annular hollow cylindrical body may be transparent to permit any legend on the ampule to be viewed visually through the hollow body.

12 Claims, 2 Drawing Sheets

SYRINGE AMPULE HOLDING DEVICE

BACKGROUND OF THE INVENTION

The present invention relates generally to syringes and devices for supporting ampules on the syringe. More particularly, this invention relates to an ampule holder adapted to be fitted onto the body of a syringe used for injecting medications into patients. The ampule holder comprises an annular hollow body for attaching to the body of the syringe and a hollow body sized to hold an ampule.

It has been customary to immediately discard used ampules after loading the medication into a syringe. This means that the person giving the injection must depend upon their memory to determine which syringe contains the desired medication when several syringes are loaded at once. When more than one syringe is loaded at a time, confusion could result and the patient could receive the wrong medication.

Moreover, many of the ampules used today are the break-open variety wherein the ampule stem is broken to gain access to the medicine. When such ampules are used, a sharp edge is created at the broken interface that could cause injury to those handling the ampule and giving the injection.

SUMMARY OF THE INVENTION

An object of the present invention is to provide an ampule holding device for holding and maintaining an empty ampule from which medication has been drawn.

Another object of the invention is to provide an ampule holder that allows the type of medication in the syringe to be determined.

It is still another object of the invention to provide an ampule holder on the body of a syringe to store a broken open ampule without exposing the patient or the nurse to the jagged glass edges of the ampule.

Generally speaking, the invention comprises an inexpensive holder adapted to fit onto or to be supported on the body of a syringe. The holder comprises an annular hollow cylindrical body having an inner circumference adapted to frictionally engage and support the outer circumference of a depleted ampule. An annular ring is attached to or formed integral with the hollow cylindrical body to position the hollow cylindrical body along the body of the syringe.

The foregoing, and other objects, advantages, and characterizing features of the present invention will become apparent from the detailed description of certain illustrated embodiments thereof, taken together with the accompanying drawings wherein like reference numerals denote like components throughout the various views.

DESCRIPTION OF THE INVENTION

Figure 1:
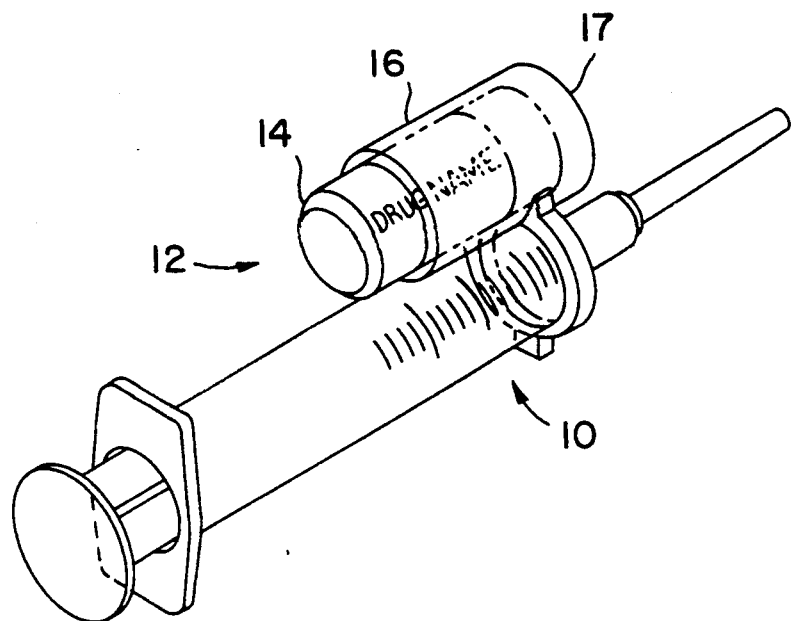
FIG. 1 is a perspective view of the ampule holder mounted on a syringe in one position.

Referring now to FIGS. 1-4 of the drawings, wherein a first embodiment of the invention is shown. A syringe 10 of usual construction is utilized to inject medication into patients. An ampule holder 12 for supporting and holding a depleted ampule 14 according to the present invention is disposed on the lower end of syringe 10. Ampule 14 is retained in an annular hollow body 16 having a closed end 17. The inner circumference of hollow body 16 may be sized to receive and retain the ampule 14 snugly within the walls of hollow body 16.

Annular hollow body 16 is held in abutting contact with the barrel of the syringe by an annular ring 18 connected to hollow body 16 by a connecting section 20. Alternatively, hollow body 16 and annular ring 18 may be formed out of one piece. In such case, connecting section 20 is unnecessary. Moreover, hollow body 16 may be formed to abut directly annular ring 18, again obviating the need for connecting section 20. An optional pull tab 22 may also be formed on the opposite side of annular ring 18 to assist in attaching the ampule holder 12 to the syringe body and gliding ample holder 12 thereon.

Figure 2:
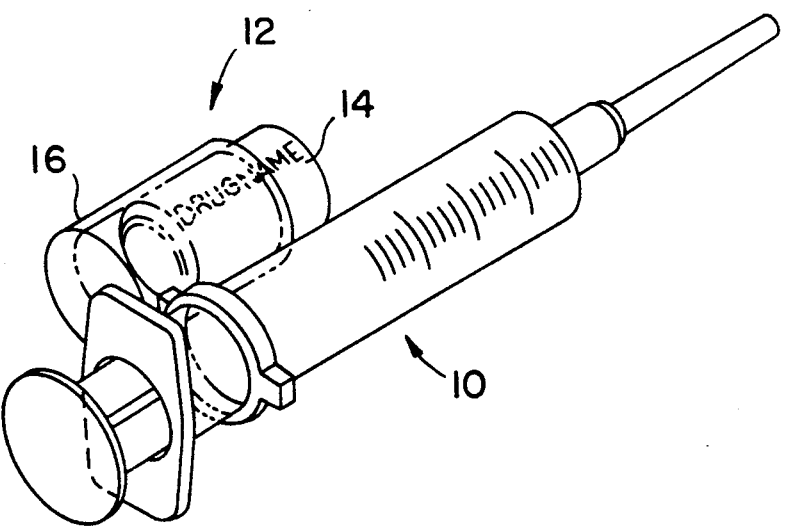
FIG. 2 is a perspective view similar to that of FIG. 1 illustrating the ampule holder in an alternative position on the body of the syringe.
Figure 3:
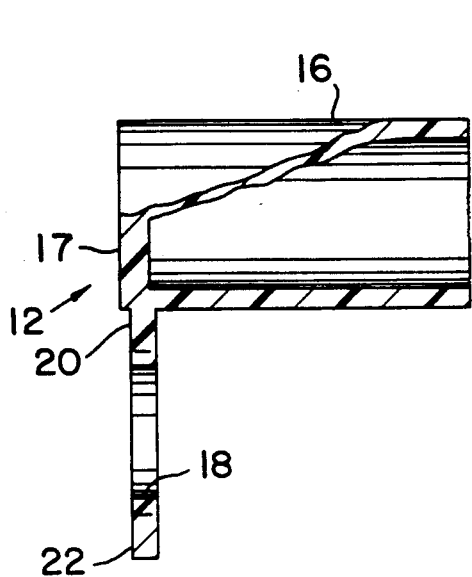
FIG. 3 is a cross sectional view of a first embodiment of the ampule holder.
Figure 4:
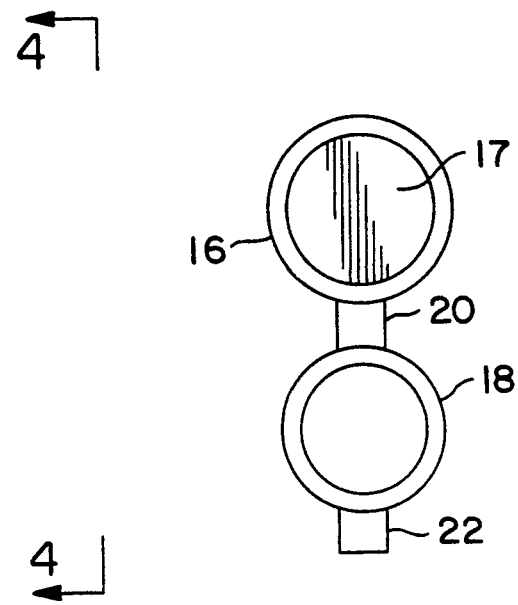
FIG. 4 is a view of the ampule holder of FIG. 3 taken along lines 4—4 of FIG. 3.

FIG. 2 shows the ampule holder along the barrel of the syringe at a different location. Ampule holder 12 may be placed at any point along syringe 10 that is convenient to the attendant or nurse.

In the embodiment shown in FIGS. 1-4, annular body 16 is closed at one end 17 so that the broken end of the ampule 14 may be inserted against closed end 17 to prevent the ampule's jagged edge from cutting the attendant, nurse, or patient.

Ampule holder 12 may be constructed of any suitable material. Plastics are especially useful for making ampule holder 12. In one preferred embodiment, annular hollow body 16 may be made of a transparent flexible plastic material that permits the legend on ampule 14 to be read through the walls of annular hollow body 16. Thus, when ampule holder 12 is in position as illustrated in FIG. 1, the nurse or attendant can easily read the drug name through the walls of clear annular hollow body 16 to know with certainty the type of medication contained in the syringe.

In use, syringe 10 is inserted through annular ring 18 and slid therethrough until ampule holder 12 is mounted in position as desired on syringe 10. If optional pull tab 22 is constructed on ampule holder 12, pull tab 22 is used in assisting to position ampule holder 12 on syringe 10. The stem from ampule 14 is then broken and syringe 10 is used to draw medication from ampule 14. Ampule 14 may be then inserted through annular hollow body 16 until the jagged edges created by the breaking of the stem are covered by closed end 17 of annular hollow body 16.

Figure 5:
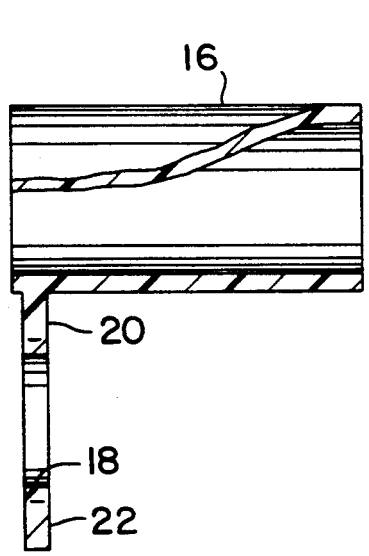
FIG. 5 is a view similar to FIG. 3 showing an alternative embodiment of the ampule holder.
Figure 6:
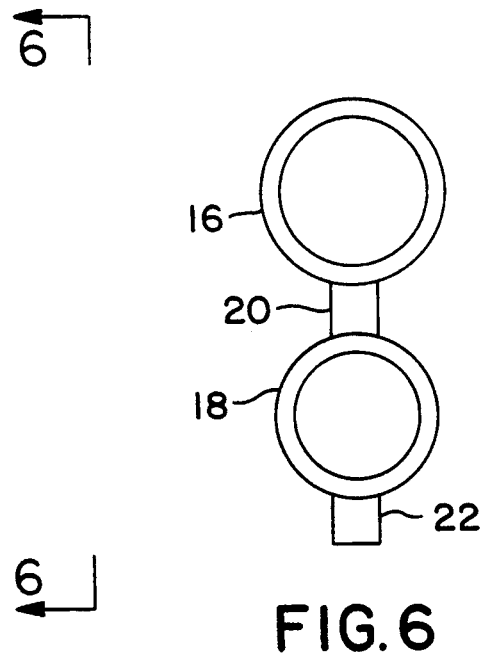
FIG. 6 is a view of the ampule holder of FIG. 5 taken along lines 6—6 of FIG. 5.

FIGS. 5 and 6 illustrate a second embodiment of the invention. In this embodiment, hollow body 16 is open on both ends. Ampule 14 may be inserted through either opening and held in place by the previously-described snug fitting arrangement.

Any of the various embodiments of the ampule holding device described herein may be constructed from materials suitable for such devices. Among those materials includes the plastics herein mentioned or any other suitable material. The holder may be made by molding or other forming processes or by any other suitable means which are well known in the art.

It will be understood that the invention is not limited to the particular ampule holders described herein nor any particular dimensions therefor. It should also be understood that any ampule holder equivalent to that described herein falls within the scope of the present invention. The embodiments described herein are merely exemplary so as to enable one of ordinary skill in the art to make and use the ampule holder. It will also be understood that while the form of the invention shown and described herein constitutes a preferred embodiment of the invention, this description is not intended to illustrate all possible forms. The words used are words of description rather than of limitation. Various changes and variations may be made to the present invention without departing from the spirit and scope of the following claims.

We claim:

1. An ampule holder supporting an ampule on the periphery of a syringe, said ampule holder comprising:
   a) a hollow body having an inner portion for supporting said ampule; and
   b) a ring attached to said hollow body, said ring having an inner circumference engaging the periphery of said syringe and supporting said hollow body on said syringe.

2. The ampule holder as set forth in claim 1 wherein said hollow body is transparent to permit visual access to any written legend appearing on said ampule when said ampule is supported by said hollow body.

3. The ampule holder as set forth in claim 1 wherein said hollow body is flexible for frictionally engaging said ampule.

4. The ampule holder as set forth in claim 1 wherein said hollow body is tubular and one end of said hollow body is closed.

5. A syringe having means for supporting an ampule thereon, said ampule supporting means comprising a hollow body, wherein said hollow body is peripherally disposed on said syringe.

6. The syringe as set forth in claim 5 wherein said hollow body has an inner circumference adapted to frictionally engage and support said ampule.

7. The syringe as set forth in claim 5 wherein said hollow body is transparent to permit visual access to any written legend appearing on said ampule.

8. The syringe as set forth in claim 5 wherein said hollow body is constructed from plastic.

9. The syringe as set forth in claim 5 wherein said hollow body is tubular and one end of said tubular hollow cylindrical body is closed.

10. The syringe as set forth in claim 5 wherein said hollow body is carried on said syringe by an annular ring attached to said hollow body.

11. An ampule holder supporting an ampule on a syringe, said ampule holder comprising:
    a) an annular hollow cylindrical body having an inner circumference for frictionally engaging and supporting said ampule, said annular hollow cylindrical body being constructed of a transparent material so that identifying marks on said ampule may be read visually when said ampule is inserted therein; and
    b) an annular ring constructed integral with said annular hollow cylindrical body, said ring having an inner circumference for engaging and supporting said annular hollow cylindrical body on the periphery of said syringe.

12. The ampule holder as set forth in claim 11 wherein said annular ring further comprises a pull tab to assist in positioning said ampule holder on said syringe.

* * * * *